(12) United States Patent
Switalski et al.

(10) Patent No.: US 6,600,559 B2
(45) Date of Patent: Jul. 29, 2003

(54) ON-LINE METHOD FOR DETECTING PARTICLE SIZE DURING A MILLING PROCESS

(75) Inventors: Steven C. Switalski, Rochester, NY (US); Donald J. Majka, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 128 days.

(21) Appl. No.: 09/815,204

(22) Filed: Mar. 22, 2001

(65) Prior Publication Data

US 2002/0176078 A1 Nov. 28, 2002

(51) Int. Cl.[7] .......................... G01N 15/02; G01N 15/06
(52) U.S. Cl. ...................... 356/336; 356/337; 356/338; 356/340; 250/574; 250/575; 250/341.8; 250/343
(58) Field of Search .................... 250/574, 575, 250/341.8, 343; 356/336, 335, 337, 338, 340

(56) References Cited

U.S. PATENT DOCUMENTS

| 4,260,258 A | * | 4/1981 | Rose et al. ................. 250/573 |
| 4,842,406 A | * | 6/1989 | VonBargen ................. 356/336 |
| 5,061,070 A | * | 10/1991 | Batchelder et al. .......... 356/491 |
| 5,343,044 A |   | 8/1994 | Sjaunja et al. .......... 250/339.09 |
| 5,633,503 A | * | 5/1997 | Kosaka .................... 250/458.1 |

OTHER PUBLICATIONS

Andrew J. O'Neil, et al., "The application of multiple linear regression to the measurement of the median particle size of drugs and pharmaceutical excipients by near–infrared spectroscopy," *The Analyst*, 1998, 123, 2297–2302.

* cited by examiner

*Primary Examiner*—Evelyn Lester
(74) *Attorney, Agent, or Firm*—Peyton C. Watkins

(57) ABSTRACT

An on-line method for detecting particle size of a liquid during a process in which there is not a correlation between low absorbance with small particle size, the method comprises the steps of measuring a plurality of reference particle sizes each associated with a particular near infrared diffuse reflectance spectrum for creating a reference infrared diffuse reflectance spectrum having high absorbance with small particle size; measuring on-line a near infrared diffuse reflectance spectrum of the liquid during the process; and determining the particle size of the on-line liquid based on correlating the on-line-measured particle size with the reference near infrared diffuse reflectance spectrum.

10 Claims, 4 Drawing Sheets

ON-LINE METHOD FOR DETECTING PARTICLE SIZE DURING A MILLING PROCESS

FIELD OF THE INVENTION

The invention relates generally to the field of particle size measurement during milling and other chemical processes, and more specifically, to an on-line measurement method during the milling process.

BACKGROUND OF THE INVENTION

Many prior art techniques are used for particle sizing, or determining the mean particle diameter or the particle size distribution. These techniques range from sorting techniques (sieving, Coulter counter), to interactance techniques (ultrasound, optical). Of the interactance techniques, optical techniques are most numerous, and typically rely on light scattering from the particles. This scatter can be time-dependent or wavelength-dependent. Many of these techniques require lasers at a single wavelength, or require light that has been filtered to provide monochromatic light. Some involve forward scatter, and others look specifically at the scatter over certain time domains for using Brownian motion of the particles to determine their sizes.

In the field of near infrared spectroscopy, diffuse reflectance spectroscopy was the first spectroscopy of major practical value (Williams, Phil and Karl Norris, "Near-Infrared Technology in the Agricultural and Food Industries", American Association of Cereal Chemists, Inc., St. Paul, Minn., 1987). This technique was applied to biological samples, especially wheat, and especially ground wheat. It was observed that the wheat powder or flour gave spectra that were dependent on the particle size of the wheat or flour. In most cases, this dependence on particle size was viewed as a problem to be overcome because the dependence on particle size made it difficult to calibrate the samples for changes in composition, such as the moisture or protein content of the wheat or flour. Many multivariate statistical techniques and algorithms have been developed and designed to reduce, compensate, or eliminate the effects of particle size on the spectra.

In some cases, the particle size dependence of the spectra has been found to be a useful effect. In pharmaceutical grinding of materials, workers have attempted to use this particle size dependence. However, there is little evidence of the use of, or any reference to, the particle size dependence of NIR diffuse reflectance spectra in liquids, slurries, emulsions, and dispersions. U.S. Pat. No. 5,343,044, Lars-Ove Sjaunja, et al., describes the measurement of aqueous fat-containing samples, such as milk, using IR (not NIR) wavelengths. The main objective is to measure the concentration of a component, but the degree of homogenization is also measured, which is an indirect measure of the mean particle size. The materials show lower absorbance with smaller particle size.

Consequently, a need exists for a method of measuring particle size in liquids, slurries, emulsions and dispersions in which there is no correlation of lower absorbance with smaller particle size.

SUMMARY OF THE INVENTION

The present invention is directed to overcoming one or more of the problems set forth above. Briefly summarized, according to one aspect of the present invention, the invention resides in an on-line method for detecting size of particles in a liquid during a process in which there is not a correlation between low absorbance with small particle size, the method comprising the steps of (a) measuring a plurality of reference particle sizes each associated with a particular near infrared diffuse reflectance spectrum for creating a reference infrared diffuse reflectance spectrum having high absorbance with small particle size; (b) measuring on-line a near infrared diffuse reflectance spectrum of the liquid during the process; and (c) determining the size of the particles of the on-line liquid based on correlating the on-line-measured particle size with the reference near infrared diffuse reflectance spectrum.

ADVANTAGEOUS EFFECT OF THE INVENTION

The present invention has the advantages of on-line measurement. This allows it to be real-time, and the result can be responded to, either by the operator of the mill, or by using the value to automatically control the mill. For example, the result can be used determine the end point of milling and to shut off the process. Additionally, the measurement is made repeatably, improving precision. Also, the results can be watched with time, showing the operation of the mill as a function of time. The curves generated from this can be used to compare operation of the mill to previous operation, and to predict the future operation of the mill on similar product.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein.

To facilitate understanding, identical reference numerals have been used, where possible, to designate identical elements that are common to the figures.

DETAILED DESCRIPTION OF THE INVENTION

Figure 1:
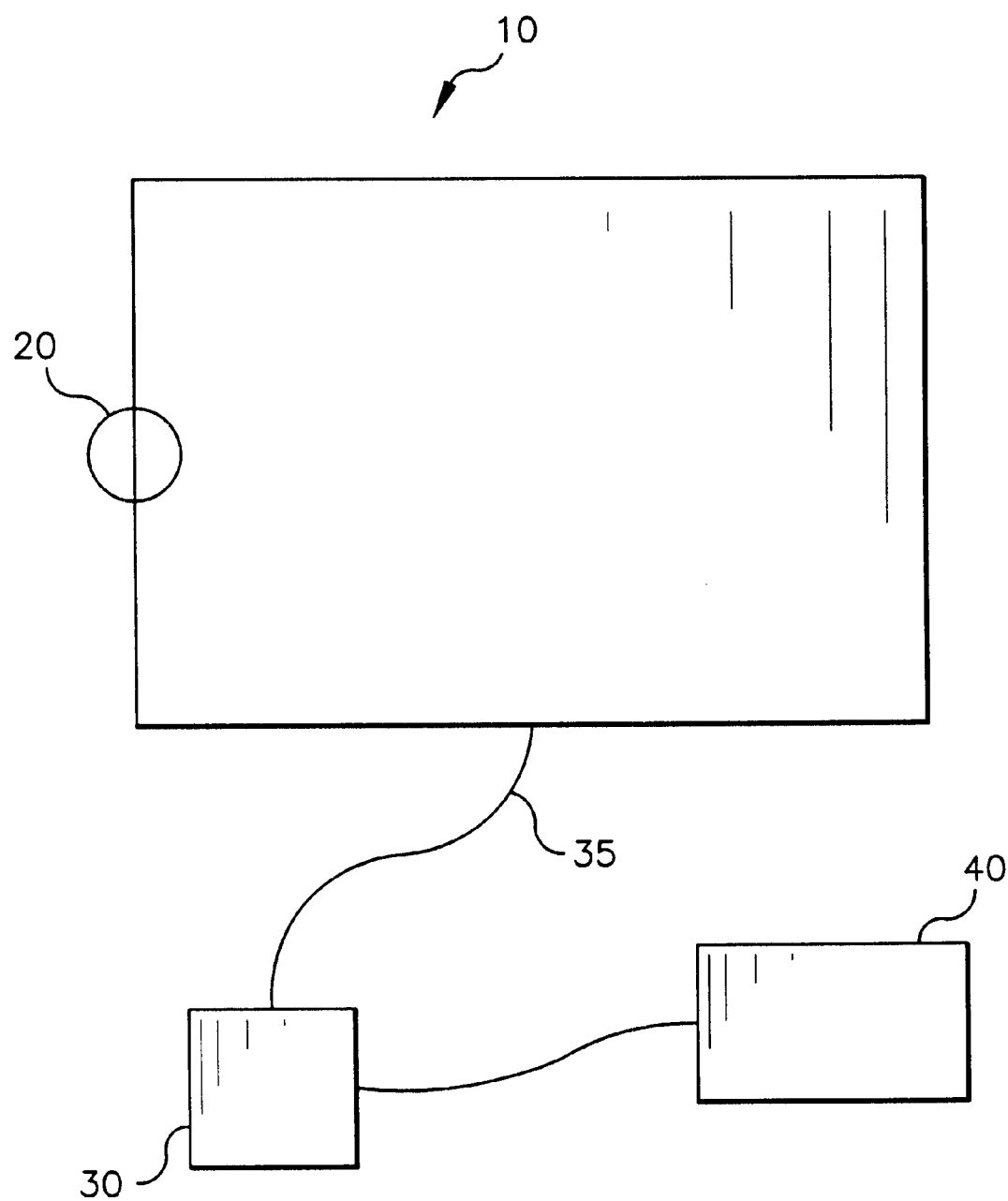
FIG. 1 is a schematic diagram of a closed-loop system of the present invention.

The present invention includes near infrared (NIR) diffuse reflectance spectroscopic technology that can be used to measure particle size either off-line, on-line, and/or in-line for a milling, photographic-chemical process. It should be understood that this invention can be used in other chemical processes. This allows for particle size monitoring, particle size determination, process monitoring, end point determination, and product/process characterization for a milling process.

Briefly summarized, the milling, photographic-chemical process of the present invention includes a closed-loop circulation system 10 through which a solution (not shown) flows. A milling device 20 is positioned in the closed-loop system for partitioning the solution flowing therethrough into smaller particles. A spectroscopy measurement device 30, such as a FOSS NIR Systems Model 5000 Process NIR Spectrophotometer, monitors the closed-loop system 10 via a fiber optic cable and diffuse reflectance probe 35 for measuring the spectroscopy of the solution. The measured data is sent to a computer system 40 where the measured data is compared to empirical data, as will be discussed in detail hereinbelow, for determining when the solution has met a predetermined particle size. As will be obvious to those skilled in the art, other embodiments are viable without departing from the scope of the invention. For example, the closed-loop system 10 may be a single vessel or container.

The present invention includes the collection of samples and the training of the spectroscopy to measure the particle size. During the milling process, samples are taken from the process and the particle size is measured along with the spectroscopy associated with the particle size. The spectra are measured in diffuse reflectance, and then processed to absorbance, for example FIG. 2, and $2^{nd}$ derivative of absorbance, for example FIG. 3. This is the preferred form of the spectra, but information can be obtained from all the intermediate steps. For example, in FIG. 2, there are illustrated five spectra taken from the milling process; each line is a spectra derived from data taken during the milling process, each of which spectra is associated with a particular mean particle size.

The resultant spectroscopy data is calibrated to the measured particle size from the collected samples. This calibration can be done with any of a number of univariate and multivariate statistical methods, such as classical least squares, multiple linear regression (MLR), partial least squares, principal component regression, etc. The present invention used MLR, mainly for simplicity and ease of adjustment of the models to shifts in process parameters, such as mixing speed, temperature, etc.

Figure 2:
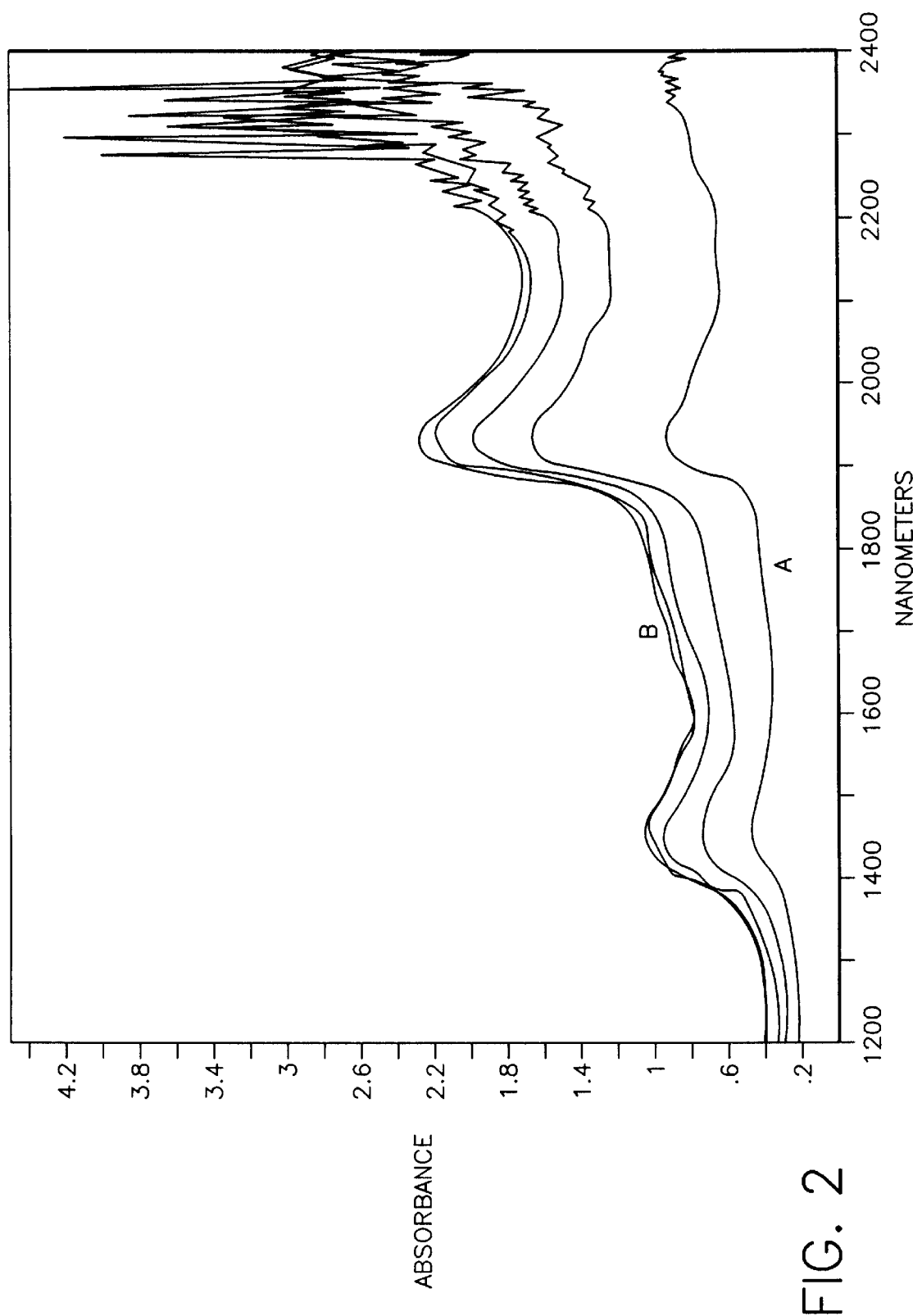
FIG. 2 is a plot of a series of NIR spectra from a milling process, showing an increase in absorbance as the particle size is decreased in the milling process.
Figure 3:
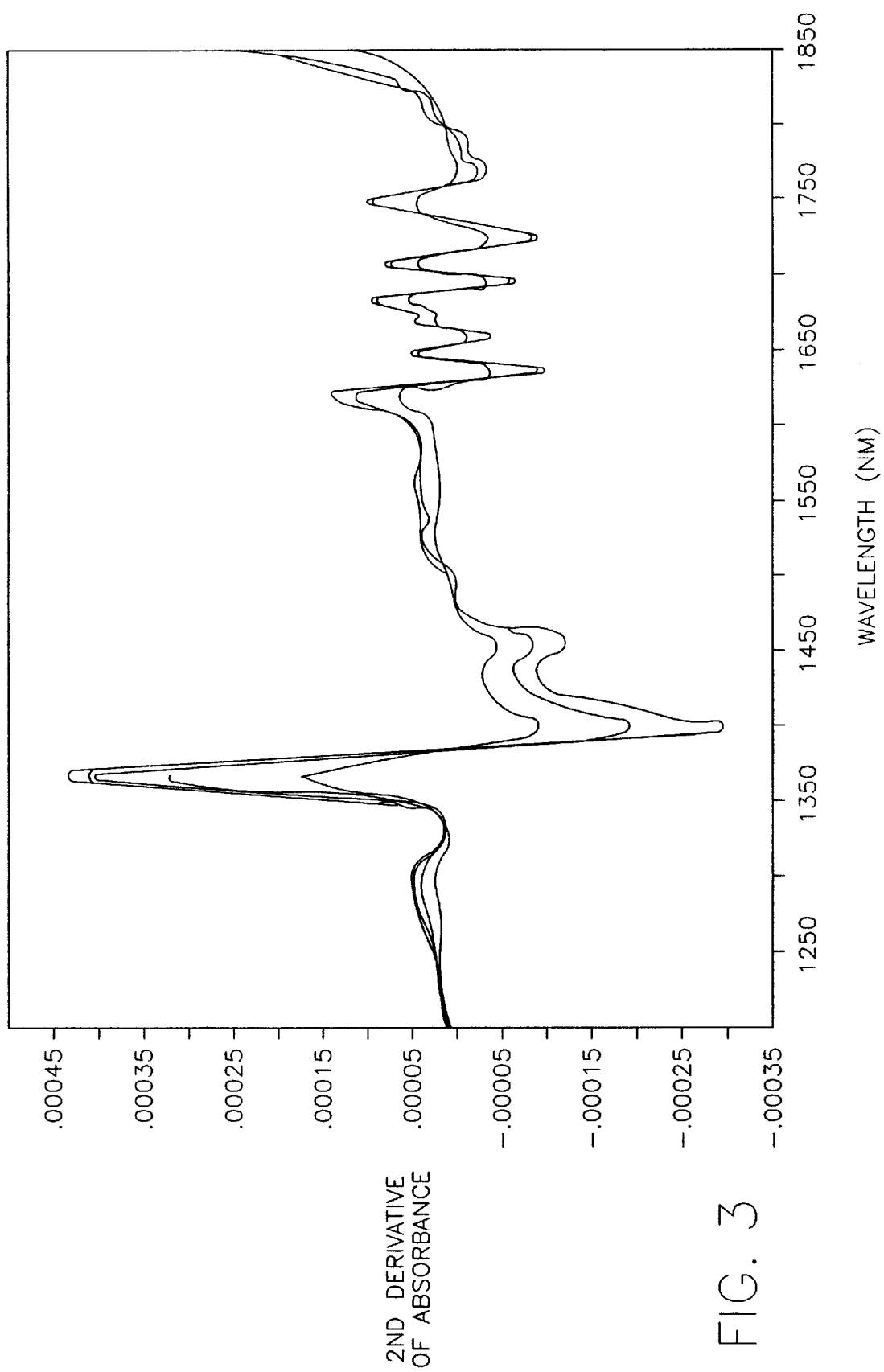
FIG. 3 is a plot of a series of $2^{nd}$ derivative of absorbance spectra from FIG. 1, for a milling process, showing the absorbance bands of the scattering particles, and the change in absorbance on both the water bands and the solid dye particles in a milling process.

Referring to FIG. 2, from the spectra, there is a correlation between the absorbance (and all the other spectra listed above) and the particle size. As the residence time in the mill increases, and the particle size decreases, the absorbance increases. Line A represents larger particle sizes, and line B represents smaller particle sizes. Although FIG. 2 illustrates a NIR spectral range from 1200 nanometers to 2400 nanometers, a range of 1100 nanometers to 2500 nanometers is useful. Those skilled in the art will recognize that the NIR spectral range is 750 nanometers to 3000 nanometers.

Figure 4:
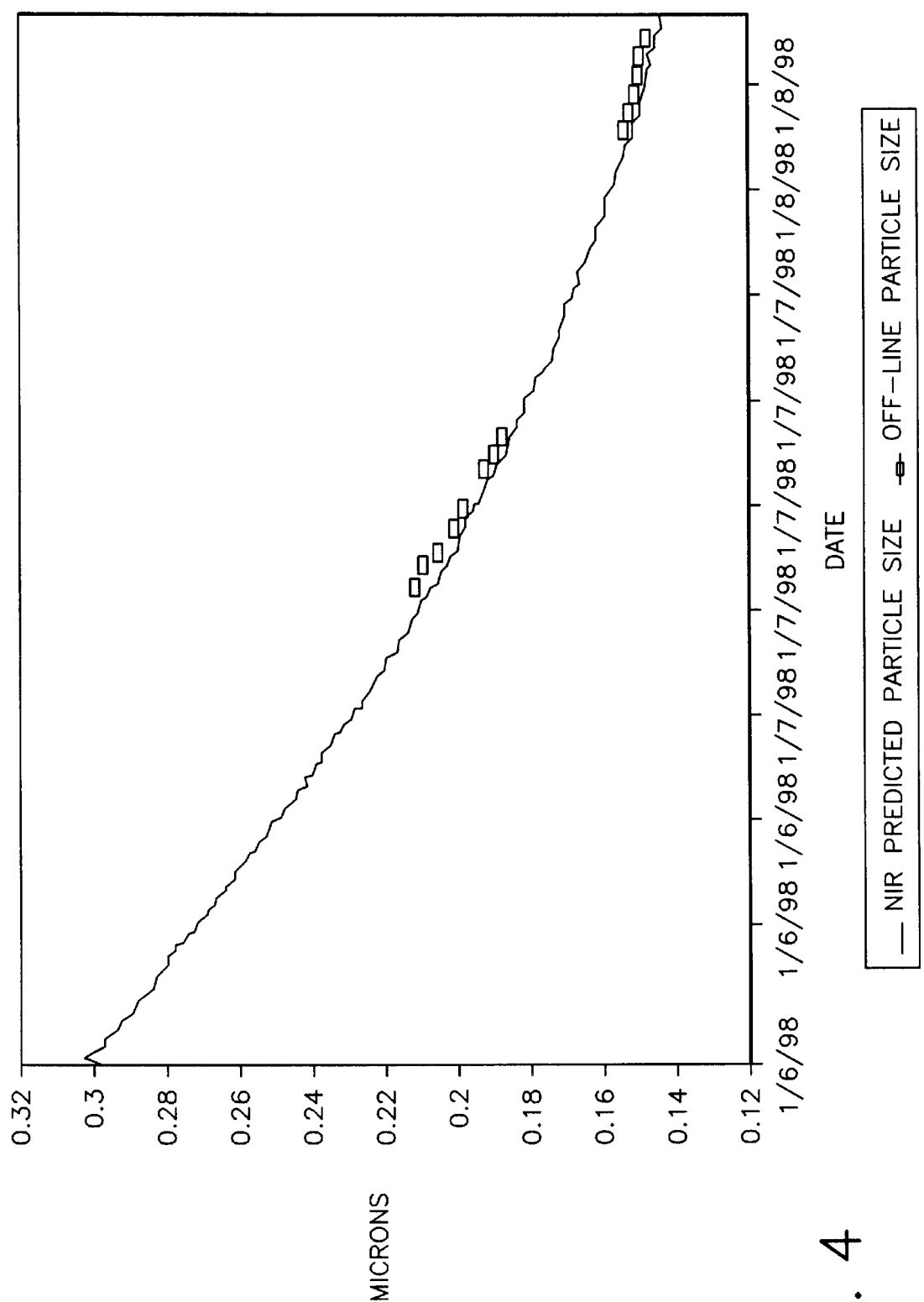
FIG. 4 is a plot of the on-line mean particle size, as predicted by the NIR diffuse reflectance technique, real-time, for a milling process, wherein the squares represent the value determined for the particle size from a sample collected from the process and measured off-line.

Once the model has been made, it can be used to predict, monitor, and follow particle size on-line. The end point (the point chosen to end the process) is also detectable with the method of the present invention, with the time and material savings of not having to take further samples for off-line measurements in subsequent batches. Referring to FIG. 4, there is shown a line representing the on-line near infrared mean particle size. The end point was detected with the NIR predicted curve, showing the real-time, on-line particle size. The squares show the value of the off-line particle size test on samples taken at a few times in the milling, especially near the end point. At the end point, the difference between the NIR on-line particle size and the off-line particle size measured on a sample was only 1 nm (0.001 microns).

The instrumentation used for measurement may be of a commercial type, for example a FOSS NIR Systems Model 5000 Process NIR Spectrophotometer. It is also instructive to note that the comparison of the measured data to the empirical data may be done by any well-known computer system.

The invention has been described with reference to a preferred embodiment; however, it will be appreciated that variations and modifications can be effected by a person of ordinary skill in the art without departing from the scope of the invention.

| PARTS LIST | |
|---|---|
| 10 | closed-loop circulation system |
| 20 | milling device |
| 30 | spectroscopy measurement device |
| 35 | diffuse reflectance probe |
| 40 | computer system |

What is claimed is:

1. A on-line method for detecting size of particles in a liquid during a process, the method comprising the steps of:
    (a) measuring a plurality of reference particle sizes each associated with a particular near infrared diffuse reflectance spectrum for creating a reference near infrared diffuse reflectance spectrum;
    (b) measuring on-line a near infrared diffuse reflectance spectrum of the liquid during the process; and
    (c) determining the size of the particles in the on-line liquid based on correlating the on-line-measured particle size with the reference near infrared diffuse reflectance spectrum.

2. The method as in claim 1, wherein the near infrared diffuse reflectance spectrum has a range substantially of 1100 nanometers to 2500 nanometers.

3. The method as in claim 1, wherein step (b) includes measuring the near infrared diffuse reflectance spectrum during an on-line, chemical process.

4. The method as in claim 1, wherein step (c) includes using a computer for the correlation of the on-line-measured particle size with the reference near infrared diffuse for reflectance spectrum.

5. The method as in claim 1, wherein step (b) includes measuring the near infrared diffuse reflectance spectrum during a milling process.

6. The method as in claim 1, wherein a spectrophotometer is used for the on-line measuring.

7. A method for detecting size of particles in a liquid, the method comprising the steps of
    (a) measuring a plurality of reference particle sizes each associated with a particular near infrared diffuse reflectance spectrum for creating a reference infrared diffuse reflectance spectrum;
    (b) measuring a near infrared diffuse reflectance spectrum of the liquid; and
    (c) determining the size of the particles in the liquid based on correlating the measured particle size with the reference near infrared diffuse reflectance spectrum.

8. The method as in claim 7, wherein the near infrared diffuse reflectance spectrum has a range substantially of 1100 nanometers to 2500 nanometers.

9. The method as in claim 7, wherein step (c) includes using a computer for the correlation of the measured particle size with the reference near infrared diffuse reflectance spectrum.

10. The method as in claim 7, wherein a spectrophotometer is used for the on-line measuring.

* * * * *